United States Patent [19]

Urakawa et al.

[11] 4,025,390

[45] May 24, 1977

[54] METHOD FOR RECOVERING UROKINASE FROM A UROKINASE-CONTAINING SOLUTION

[75] Inventors: Masaharu Urakawa; Hiroshi Sumiyama, both of Hitachi, Japan

[73] Assignee: Hitachi Chemical Company, Ltd., Tokyo, Japan

[22] Filed: Apr. 13, 1976

[21] Appl. No.: 676,489

[30] Foreign Application Priority Data

Apr. 18, 1975 Japan .............................. 50-47099

[52] U.S. Cl. ............................................. 195/66 B
[51] Int. Cl.² ........................................ C07G 7/026
[58] Field of Search ............. 195/66 B, 66 R, 66 A

[56] References Cited

UNITED STATES PATENTS 3,723,251   3/1973   Ogawa et al. ..................... 195/66 B

*Primary Examiner*—Lionel M. Shapiro
*Attorney, Agent, or Firm*—Flynn & Frishauf

[57] ABSTRACT

A method for recovering urokinase which comprises bringing a urokinase-containing solution into contact with at least one compound selected from a group consisting of cyanoalkyl polysaccharide, cyanoalkyl modified-polysaccharide and cyanoalkyl polyvinyl alcohol to subject urokinase to adsorption and then eluting the urokinase from the adsorbate.

7 Claims, No Drawings

METHOD FOR RECOVERING UROKINASE FROM A UROKINASE-CONTAINING SOLUTION

This invention relates to a method for recovering urokinase from a urokinase-containing solution. More particularly, this invention relates to a method for recovering urokinase of high purity which comprises bringing a urokinase-containing solution into contact with at least one compound selected from a group consisting of cyanoalkyl polysaccharide, cyanoalkyl modified-polysaccharide and cyanoalkyl polyvinyl alcohol to subject urokinase to adsorption and then eluting the urokinase from the adsorbate. The compounds described above are novel adsorbents for recovering urokinase.

Urokinase is a plasminogen activator which is found in human urine in trace amounts. It is a potent, blood clot lysing agent and highly purified urokinase has been used clinically for the treatment of thromboembolic disorders.

In order to recover urokinase from a urokinase-containing solution such as urine, several methods such as ultrafiltration, precipitation method with a heavy metal compound (U.S. Pat. No. 2,961,382), adsorption method with silica gel, ion exchanger (U.S. Pat. No. 2,983,647), etc., have been applied for the purpose. But, these methods can hardly give urokinase of high purity in high yields.

We have found that urokinase can be adsorbed selectively by cyanoalkyl polysaccharide, cyanoalkyl modified-polysaccharide (both abbrevated as CAS hereinafter) or cyanoalkyl polyvinyl alcohol (abbreviated as CAP hereinafter), and accomplished the present invention.

In the present invention, a urokinase-containing solution is brought into contact with CAS or CAP to subject urokinase to adsorption and then the urokinase adsorbed is eluted from the adsorbate.

In the present invention, a urokinase-containing solution is, for example, urine or a partially purified impure solution of urokinase such as a solution obtained by the conventional purifying methods described above.

The adsorbents of the present invention for the recovery of urokinase are cyanoalkyl polysaccharides such as cyanoalkyl cellulose, cyanoalkyl dextran, etc., cyanoalkyl modified-polysaccharide such as cyanoalkyl dextran closslinked with epichlorohydrin etc. for example, Sephadex (trade-mark, Aktiebolaget Pharmacia), and cyanoalkyl polyvinyl alcohol. Cyanoalkyl polysaccharide or modified-polysaccharide, or cyanoalkyl polyvinyl alcohol is derived from a polysaccharide, modified-polysaccharide or polyvinyl alcohol, respectively, according to a known method, for example, by cyanoethylation thereof with acrylonitrile or methacrylonitrile in the presence of an alkali as a catalyst.

CAS and CAP of the present invention are both water-insoluble. The cyanoalkyl group of the adsorbent of the present invention represents a cyano-lower-alkyl group having 2 to 4 carbon atoms including the carbon atom of cyano group. Examples of the group are a cyanomethyl group (—CH$_2$CN), a cyanoethyl group (—CH$_2$CH$_2$CN), 2-cyanopropyl group

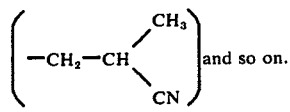

and so on.

In the method of the present invention, a urokinase-containing solution is brought into contact with CAS or CAP to subject urokinase to adsorption selectively. At this time, the pH value of the solution is adjusted to 4.5–7.5, preferably to 5.0–6.5. In order to recover urokinase from urine more conveniently, it is preferable to pretreat the urine by adjusting the pH thereof to 7.5–9.5 and removing the resulting precipitate before contacting the urine with CAS or CAP.

To elute the urokinase adsorbed from the adsorbate, an aqueous solution of alkali or basic compound is employed. Examples of an alkali or basic compound are sodium carbonate, potassium carbonate, sodium hydroxide, potassium hydroxide or ammonia. Preferably, the adsorbate is subjected to a elution process, using for the elution agent an aqueous solution having such a pH that the resulting eluate will have a pH between 9 and 11.5. Since an aqueous solution of ammonia has an effect to stabilize urokinase, it is most suitable as an eluting agent. It is more preferably used at a concentration of about 4% by weight. According to conventional procedures, the eluate is neutralized, salted out with sodium sulfate, ammonium sulfate, sodium chloride, etc., (or subjected to isoelectric precipitation) to precipitate urokinase, dialyzed and freeze-dried to give urokinase in solid form.

As described above and will be illustrated below, the present invention provides a method for the recovery of urokinase in high yield and purity with a small amount of a novel adsorbent, CAS or CAP. The adsorbents of the present invention can be used repeatedly and so are economical. The present invention can be applied to recover urokinase not only from urine itself but also from other urokinase-containing solutions.

This invention will further be illustrated by the following non-limitative examples.

EXAMPLE 1

To 100 l. of fresh human urine obtained from many normal persons were added a 40% solution of sodium hydroxide to adjust the pH value of the urine to 8.5. The resulting precipitate was removed and the pH value of the supernatant was adjusted to 6.0 with 6 N hydrochloric acid. To the solution was added 200 g. of cyanoethyl cellulose. This was obtained by dipping cyanoethylated paper into water (available from TOMOEGAWA Paper Manuf. Co., Ltd.), subjecting it to mixing by a mixer until it was reduced to pulp, sufficient washing with water and dehydration. The mixture was stirred for 30 min. and the cyanoethyl cellulose was collected by centrifugation. The cyanoethyl cellulose thus collected was then introduced into 3 l. of 4% aqueous solution of ammonia to elute the adsorbed urokinase. The eluate was neutralized with 6 N sulfuric acid and ammonium sulfate was added thereto as much as 60% saturation. After standing overnight at 4° C, the precipitate was collected, dissolved in distilled water and subjected to dialysation against water at 4° C overnight. The dialyzed solution was freeze-dried to give 1×10$^4$ IU of urokinase per liter of starting urine in total, which corresponds to a 90% yield based on the amount of urokinase in the starting urine calculated according to a reported urokinase-content, the specific activity of which was 3000 IU/mg. (IU is an abbreviation of International Unit.)

EXAMPLE 2

The pH value of 100 l. of fresh human urine employed in Example 1 was adjusted to 8.5 with 40% solution of sodium hydroxide. The resulting precipitate was removed and the pH value of the remaining solution was adjusted to 6.0 with 6 N hydrochloric acid. Subsequently, was added thereto 200 g. of cyanoethyl polyvinyl alcohol, which was obtained by cyanoethylation of polyvinyl alcohol with acrylonitrile in the presence of sodium hydroxide as a catalyst. And the mixture was stirred for 30 min. The cyanoethyl polyvinyl alcohol which adsorbed urokinase was collected and introduced into 3 l. of a 4% aqueous solution of ammonia to elute the adsorbed urokinase. The eluate was neutralized with 6 N sulfuric acid and ammonium sulfate was added thereto as much as 60% saturation. After standing overnight at 4° C, the precipitate was collected, dissolved in 50 cc. of distilled water and subjected to dialysation against water at 4° C overnight. The solution dialyzed was freeze-dried to give $9.4 \times 10^3$ IU of urokinase per liter of starting urine which corresponds to a 85% yield, the specific activity of which was 3500 IU/mg.

REFERENTIAL EXAMPLE 1

The pH value of 2 l. of human urine employed in Example 1 was adjusted to 8.5 with an aqueous solution of sodium hydroxide. After removing the resulting precipitate, the pH value of the remaining solution was adjusted to 6.0. Then, the solution was contacted with 20 ml. of silica gel to recover urokinase. The silica gel was washed with water sufficiently and the urokinase adsorbed was eluted out and recovered. The amount of urokinase recovered was $8.9 \times 10^3$ IU per liter of starting urine which corresponds to a 80% yield. The specific activity was 1200 IU/mg.

REFERENTIAL EXAMPLE 2

To 2 l. of human urine employed in Example 1 was added 100 ml. of 50% aqueous solution of zinc chloride and the resulting precipitate was collected by centrifugation. To the precipitate was added 200 ml. of 10% aqueous solution of sodium phosphate (monobasic) and the mixture was stirred to give a precipitate of zinc phosphate. The zinc phosphate was removed by filtration and the filtrate was concentrated and freeze-dried to give urokinase as a solid form. The amount of urokinase recovered was $1.06 \times 10^4$ IU per liter of starting urine which corresponds to a 95% yield. The specific activity was 3.5 IU/mg.

As is clear from the above results, the urokinase obtained according to the present procedure has an extremely high specific activity in comparison with those obtained by the conventional methods. The recovery of urokinase is also high.

What is claimed is:

1. A method for recovering urokinase which comprises bringing a urokinase-containing solution into contact with at least one compound selected from the group consisting of cyanoalkyl polysaccharide, cyanoalkyl modified-polysaccharide and cyanoalkyl polyvinyl alcohol to subject urokinase to adsorption and then eluting the urokinase from the adsorbate, said cyanoalkyl group being a cyano-lower-alkyl group having from 2 to 4 carbon atoms including the carbon atom of the cyano group.

2. The method of claim 1, wherein said polysaccharide and modified-polysaccharide are cellulose, dextran and dextran cross-linked with epichlorohydrin.

3. The method of claim 1, wherein said cyano-lower-alkyl group is cyanoethyl.

4. The method of claim 1, wherein said adsorbing operation is conducted at a pH range of from 4.5 to 7.5.

5. The method of claim 4, wherein said pH value is from 5.0 to 6.5.

6. The method of claim 1, wherein said eluting operation is conducted using for the elution agent an aqueous solution of alkali having such a pH value that the resulting eluate has a pH of from 9 to 11.5.

7. The method of claim 6, wherein said alkali solution is about 4% by weight aqueous solution of ammonia.

* * * * *